United States Patent [19]

Sasaki et al.

[11] Patent Number: 5,248,826
[45] Date of Patent: Sep. 28, 1993

[54] POLYETHER AMINE COMPOUNDS

[75] Inventors: Masaomi Sasaki, Susono; Tamotsu Aruga, Mishima; Tomoyuki Shimada, Numazu, all of Japan

[73] Assignee: Ricoh Company, Ltd., Tokyo, Japan

[21] Appl. No.: 921,203

[22] Filed: Jul. 29, 1992

Related U.S. Application Data

[62] Division of Ser. No. 626,906, Dec. 13, 1990, Pat. No. 5,158,850.

[30] Foreign Application Priority Data

Dec. 15, 1989 [JP] Japan ................... 1-325409
Dec. 28, 1989 [JP] Japan ................... 1-342793

[51] Int. Cl.$^5$ ........................................... C07C 217/76
[52] U.S. Cl. .................... 564/307; 564/384; 564/391; 564/434; 564/443
[58] Field of Search ............ 564/384, 391, 307, 434, 564/443

[56] References Cited

U.S. PATENT DOCUMENTS 3,862,226 1/1975 Harfenist ........................ 564/153

OTHER PUBLICATIONS

Morigaki et al., Chemical Abstracts, vol. 115 (1991) 194126g.
Morigaki et al., Chemical Abstracts, vol. 114 (1990) 111784a.
Satomura et al, Chemical Abstracts, vol. 109 (1988) 219667a.
Chun-Chieh et al, Chemical Abstracts, vol. 54 (1960) 5528g.

*Primary Examiner*—Richard L. Raymond
*Attorney, Agent, or Firm*—Oblon, Spivak, McClelland, Maier & Neustadt

[57] ABSTRACT

An electrophotographic photoconductor comprising an electroconductive support and a photoconductive layer formed thereon comprising as an effective component at least one polyether compound represented by formula (I):

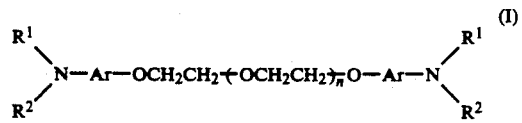

wherein Ar represents a phenylene group or a biphenylene group; $R^1$ and $R^2$ each represent an alkyl group which may have a substituent, or an aryl group which may have a substituent; and n is an integer of 1 to 4. Furthermore, charge transporting material comprising the above polyether compound, polyether compounds having formula (II) for use in the electrophotographic photoconductor and a method of preparing the same are disclosed,

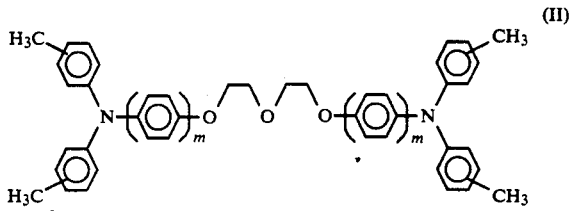

wherein m is an integer of 1 or 2.

3 Claims, 4 Drawing Sheets

POLYETHER AMINE COMPOUNDS

This is a division of application Ser. No. 07/626,906, filed on Dec. 13, 1990, now U.S. Pat. No. 5,158,850.

BACKGROUND OF THE INVENTION

1. Field of the Invention

The present invention relates to polyether compounds and an electrophotographic photoconductor comprising a photoconductive layer containing one polyether compound overlaid on an electroconductive support.

2. Discussion of Background

Conventionally, inorganic materials such as selenium, cadmium sulfide and zinc oxide are used as a photoconductive material of an electrophotographic photoconductor in the electrophotographic process. The above-mentioned electrophotographic process is one of the image forming processes, through which the surface of the photoconductor is charged uniformly in the dark to a predetermined polarity, for instance, by corona charge The uniformly charged photoconductor is exposed to a light image to selectively dissipate the electrical charge of the exposed areas, so that a latent electrostatic image is formed on the photoconductor. The thus formed latent electrostatic image is developed by a developer comprising a coloring agent such as a dye and a pigment, and a binder agent such as a polymeric material, to a visible image.

Fundamental characteristics required for the photoconductor for in such an electrophotographic process are: (1) chargeability to an appropriate potential in the dark, (2) minimum dissipation of electrical charge in the dark, and (3) rapid dissipation of electrical charge when exposed to light.

However, while the above-mentioned inorganic materials have many advantages, they have several shortcomings from the viewpoint of practical use.

For instance, a selenium photoconductor, which is widely used at present, satisfies the above-mentioned requirements (1) to (3) completely, but it has the shortcomings that its manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by coating a dispersion of cadmium sulfide particles and zinc oxide particles in a binder resin on a support. However, they are poor in mechanical properties, such as surface smoothness, hardness, tensile strength and wear resistance. Therefore, they cannot be used in the repeated operation, as they are.

To solve the problems of the inorganic materials, various electrophotographic photoconductors employing organic materials are proposed recently and some are still put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as described in Japanese Patent Publication 48-2658; a photoconductor comprising as the main component an organic pigment, as described in Japanese Laid-Open Patent Application 47-37543; a photoconductor comprising as the main component an eutectic crystal complex of a dye and a resin, as described in Japanese Laid-Open Patent Application 47-10735; a photoconductor prepared by sensitizing a triphenylamine compound with a sensitizer pigment, as described in U.S. Pat. No. 3,180,730; a photoconductor comprising an amine derivative as a charge transporting material, as described in Japanese Laid-Open Patent Application 57-195254; a photoconductor comprising poly-N-vinylcarbazole and an amine derivative as charge transporting materials, as described in Japanese Laid-Open Patent Application 58-1155; and a photoconductor comprising a polyfunctional tertiary amine compound, in particular benzidine compound, as a photoconductive material, as described in U.S. Pat. No. 3,265,496, Japanese Patent Publication 39-11546 and Japanese Laid-Open Patent Application 53-27033.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements for use in electrophotography.

SUMMARY OF THE INVENTION

It is therefore a first object of the present invention to provide an electrophotographic photoconductor free from the conventional shortcomings, which can completely satisfy all the requirements in the electrophotographic process, including high durability, and can be easily manufactured at relatively low cost.

A second object of the present invention is to provide a photoconductive material for use in the above-mentioned electrophotographic photoconductor.

A third object of the present invention is to provide polyether compounds employed as photoconductive materials in the electrophotographic photoconductor.

A fourth object of the present invention is to provide intermediate compounds for preparing the above polyether compounds.

A fifth object of the present invention is to provide a method of preparing the above polyether compounds.

The first object of the present invention can be achieved by an electrophotographic photoconductor comprising an electroconductive support and a photoconductive layer formed thereon comprising as an effective component at least one polyether compound represented by formula (I):

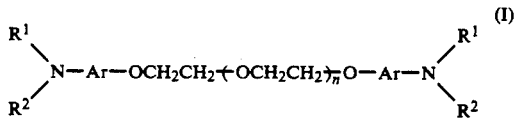

wherein Ar represents a phenylene group biphenylene group; $R^1$ and $R^2$ each represent an alkyl group which may have a substituent, or an aryl group which may have a substituent; and n is an integer of 1 to 4.

The second object of the present invention can be achieved by a material comprising a polyether compound represented by the above formula (I).

The third object of the present invention can be attained by polyether compounds having formula (II):

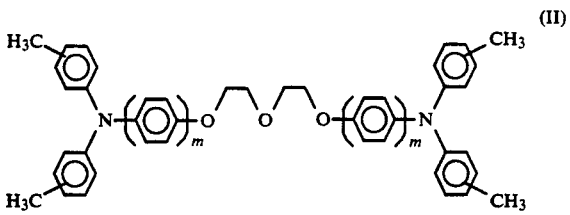

wherein m is an integer of 1 or 2.

The fourth object of the present invention can be achieved by 3-oxapentane compounds having formula (III):

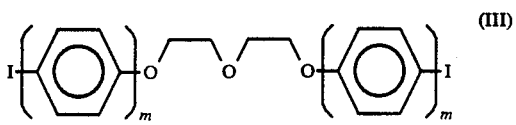

wherein m is an integer of 1 or 2.

The fifth object of the present invention is attained by subjecting a 3-oxapentane compound of formula (III) and a dimethyl diphenyl amine derivative of formula (IV) to the Ullmann coupling reaction in the following reaction scheme:

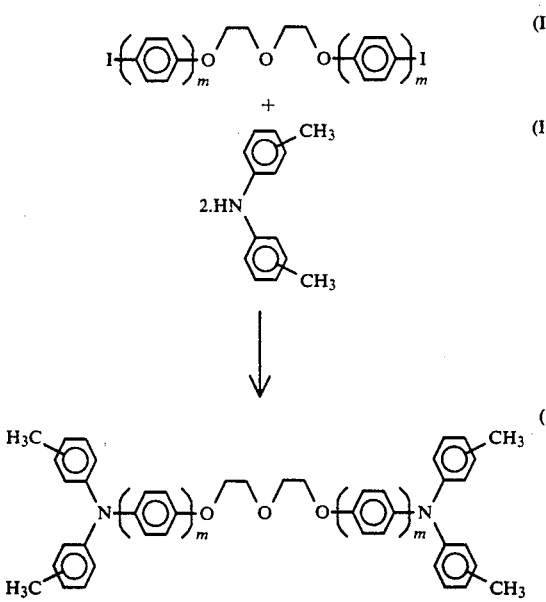

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
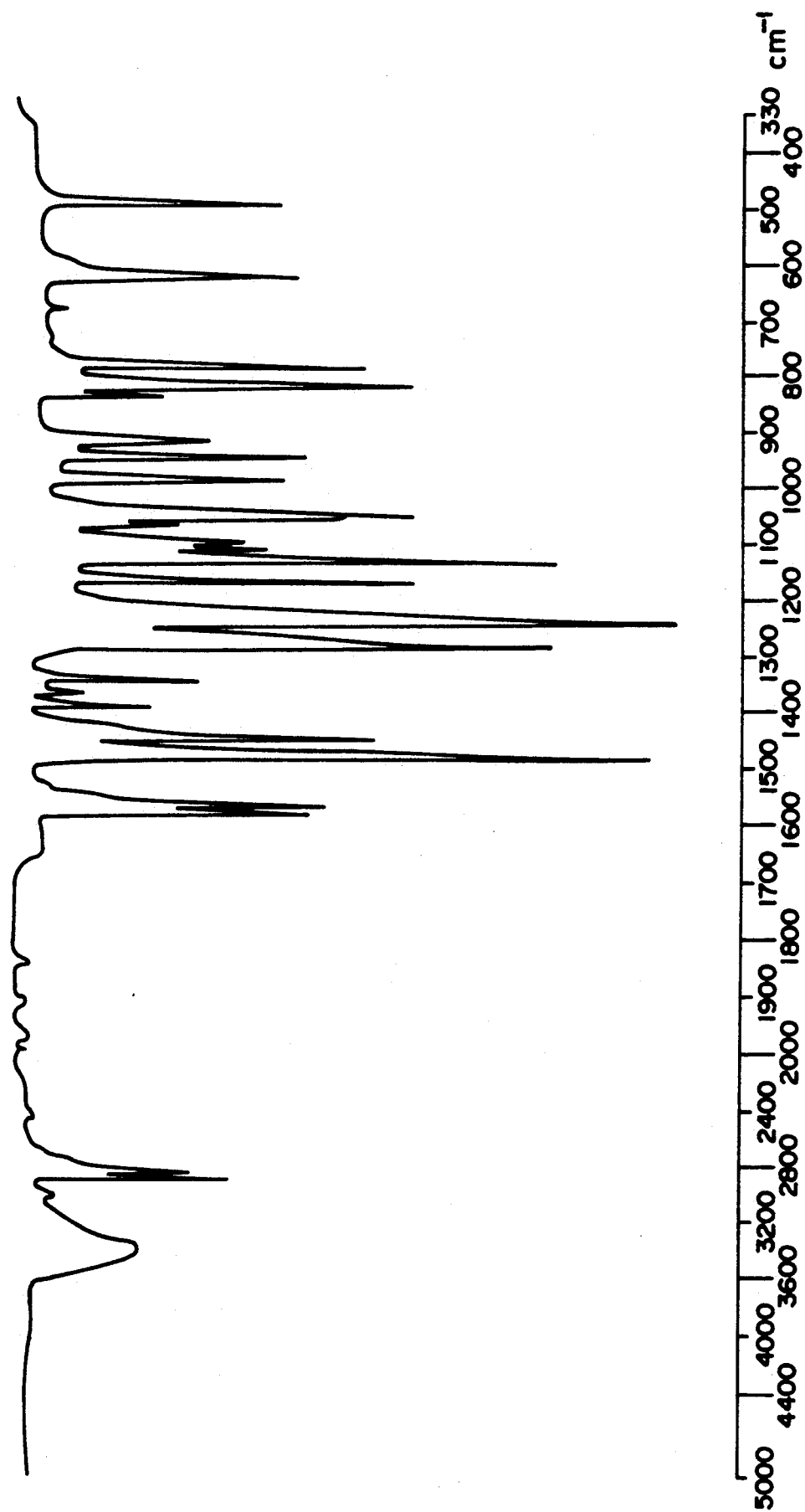
FIGS. 1 and 2 are the IR spectra of 3-oxapentane compounds, serving as the intermediate materials for preparing the polyether compounds according to the present invention.

An electrophotographic photoconductor according to the present invention comprises an electroconductive support and a photoconductive layer formed thereon, comprising at least one of polyether compounds of formula (I):

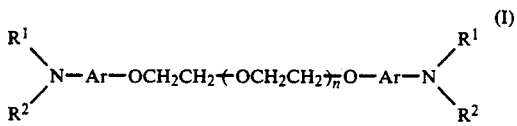

wherein Ar represents a phenylene group or a biphenylene group; $R^1$ and $R^2$ each represent an alkyl group which may have a substituent, or an aryl group which may have a substituent; and n is an integer of 1 to 4.

When $R^1$ and $R^2$ each represent an aryl group, examples of the aryl group include aromatic groups, such as a phenyl group, a biphenyl group, a terphenyl group and a naphthyl group.

Examples of the substituent of the aryl group in the formula (I) are as follows:

(1) A halogen, a cyano group and a nitro group.

(2) An alkyl group, in particular a straight-chain or branched-chain alkyl group having 1 to 12 carbon atoms, more preferably an alkyl group having 1 to 8 carbon atoms, and further preferably an alkyl group having 1 to 4 carbon atoms. The above alkyl group may have a substituent such as a fluorine atom, an hydroxyl group, a cyano group, an alkoxyl group having 1 to 4 carbon atoms, and a phenyl group which may have a substituent such as a halogen, an alkyl group having 1 to 4 carbon atoms or an alkoxyl group having 1 to 4 carbon atoms.

Specific examples of the above alkyl group include a methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

(3) An alkoxyl group represented by —$OR^3$, in which $R^3$ represents the same alkyl group as defined in (2).

Specific examples of the above alkoxyl group include a methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group, 4-methylbenzyloxy group and trifluoromethoxy group.

(4) An aryloxy group, in which an aryl group represents, for example, a phenyl group and a naphthyl group. The above aryloxy group may have a substituent such as an alkoxyl group having 1 to 4 carbon atoms, an alkyl group having 1 to 4 carbon atoms or a halogen.

Specific examples of the above aryloxy group include a phenoxy group, 1-naphthyloxy group, 2-naphthyloxy group, 4-methylphenoxy group, 4-methoxyphenoxy group, 4-chlorophenoxy group and 6-methyl-2-naphthyloxy group. (5) An alkylmercapto group represented by $-SR^4$, in which $R^4$ represents the same alkyl group as defined in (2).

Specific examples of the above alkylmercapto group include a methylthio group, ethylthio group, phenylthio group and p-methylphenylthio group.

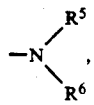

in which $R^5$ and $R^6$ independently represent hydrogen, the same alkyl group as defined in (2) or aryl group. As the aryl group, a phenyl group, biphenyl group or naphthyl group can be employed, which may have a substituent such as an alkoxyl group having 1 to 4 carbon atoms, an alkyl group having 1 to 4 carbon atoms or a halogen $R^5$ and $R^6$ may form a ring in combination, or in combination with carbon atoms on the aryl group.

Specific examples of the above

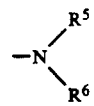

include an amino group, diethylamino group, N-methyl-N-phenylamino group, N,N-diphenylamino group, N,N-di(p-tolyl)amino group, dibenzylamino group, piperidino group, morpholino group and julolidyl group.

(7) An alkylenedioxy group or alkylenedithio group such as a methylenedioxy group or methylenedithio group.

When $R^1$ and $R^2$ each represent an alkyl group in formula (I), the same alkyl group as defined in the above (2) can be employed.

Specific examples of the polyether compounds according to the present invention are shown in the following Table 1.

TABLE 1

$$\begin{array}{c} R^1 \\ \diagdown \\ N-Ar-OCH_2CH_2(\!-\!OCH_2CH_2)_{\overline{n}}O-Ar-N \\ \diagup \\ R^2 \end{array} \begin{array}{c} R^1 \\ \diagdown \\ \diagup \\ R^2 \end{array} \quad (I)$$

| Compound No. | Ar | $R^1$ | $R^2$ | n |
|---|---|---|---|---|
| 1 | —⌬— | —⌬ | —⌬ | 1 |
| 2 | " | —CH₃ | —⌬ | 1 |
| 3 | " | —CH₂⌬ | —⌬ | 1 |
| 4 | " | —⌬—CH₃ | —⌬—CH₃ | 1 |
| 5 | " | —⌬—OCH₃ | —⌬—OCH₃ | 1 |
| 6 | " | —⌬—OCH₃ | —⌬ | 1 |
| 7 | " | —⌬—⌬ | —⌬ | 1 |

TABLE 1-continued $$\begin{matrix} R^1 \\ \phantom{R}\diagdown \\ N-Ar-OCH_2CH_2(OCH_2CH_2)_nO-Ar-N \\ \phantom{R}\diagup \\ R^2 \end{matrix} \begin{matrix} R^1 \\ \diagup \\ \phantom{N} \\ \diagdown \\ R^2 \end{matrix} \quad (I)$$

| Compound No. | Ar | R¹ | R² | n |
|---|---|---|---|---|
| 8 | " | 1-naphthyl | phenyl | 1 |
| 9 | " | 4-methylphenyl | 4-methylphenyl | 2 |
| 10 | " | 4-methylphenyl | 4-methylphenyl | 3 |
| 11 | " | 4-methylphenyl | 4-methylphenyl | 4 |
| 12 | 4,4'-biphenylene | 4-methylphenyl | 4-methylphenyl | 1 |
| 13 | " | phenyl | phenyl | 1 |
| 14 | " | 4-methylphenyl | phenyl | 1 |
| 15 | " | 4-methoxyphenyl | 4-methoxyphenyl | 1 |
| 16 | " | 4-methylphenyl | —CH₃ | 1 |
| 17 | " | 4-methylphenyl | 4-methylphenyl | 2 |
| 18 | " | 4-methylphenyl | 4-methylphenyl | 3 |

The polyether compounds of formula (I) according to the present invention can be obtained by allowing a compound having formula (V) to react with a halogenide having formula (VI).

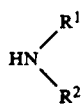

(V)

wherein R¹ and R² are the same as previously defined in formula (I).

$$X-Ar-OCH_2CH_2-(OCH_2CH_2)_n-O-Ar-X \quad (VI)$$

wherein Ar and n are the same as previously defined in formula (I), and X represents a halogen.

More specifically, polyether compounds No. 4 and No. 12 in Table 1 can be obtained by allowing a 3-oxapentane compound having formula (III) to react with a dimethyldiphenylamine derivative of formula (IV) by the Ullmann coupling reaction in accordance with the following reaction scheme:

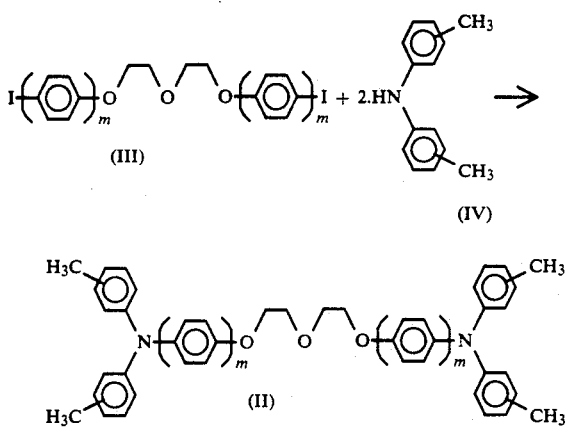

Namely, a 3-oxapentane compound of formula (III) is allowed to react with a dimethyldiphenylamine derivative of formula (IV) in a solvent in a stream of nitrogen at about 150° to 250° C. in the presence of copper particles, copper oxide or copper halogenide, with an alkaline salt or alkaline material added thereto in a sufficient amount for neutralizing hydrogen halogenide generated in the course of the reaction. In this case, the solvent may not be used in the reaction.

Examples of the above-mentioned alkaline salt used in the reaction are sodium carbonate and potassium carbonate; and examples of the alkaline material are sodium hydroxide and other caustic alkaline materials. Examples of the solvent used in the reaction are nitrobenzene, dichlorobenzene, quinoline, N,N-dimethylformamide, dimethyl sulfoxide, N-methylpyrrolidone and 1,3-dimethyl-2-imidazolidinone.

The above-mentioned 3-oxapentane compound of formula (III) can be prepared by refluxing a mixture of a 1,5-dichloro-3-oxapentane and a compound represented by the following formula [VII] in water or an organic solvent in the presence of a caustic alkaline material such as sodium hydroxide and potassium hydroxide. In this case, benzene, toluene, N,N-dimethylformamide, dimethyl sulfoxide, ethanol and n-butanol can be used as the above-mentioned organic solvent.

(VII)

wherein m is an integer of 1 or 2.

The polyether compounds according to the present invention, which are remarkably effective as photoconductive materials in the electrophotographic photoconductor, are optically or chemically sensitized with a sensitizer such as a dye or Lewis acid. In addition, the polyether compounds effectively function as a charge transporting material in a function-separating type electrophotographic photoconductor where an organic or inorganic pigment serves as a charge generating material.

In the photoconductors according to the present invention, at least one polyether compound of the formula (I) is contained in the photoconductive layers 2, 2a, 2b, 2c and 2d. The polyether compounds can be employed in different ways, for example, as shown in FIGS. 4 through 8.

Figure 4:
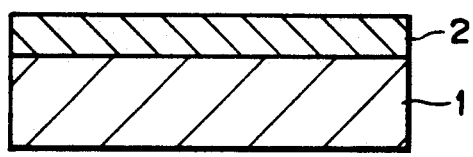
FIG. 4 is a schematic cross-sectional view of a first example of an electrophotographic photoconductor according to the present invention.

In the photoconductor as shown in FIG. 4, a photoconductive layer 2 is formed on an electroconductive support 1, which photoconductive layer 2 comprises a polyether compound, a sensitizing dye and a binder agent (binder resin). In this photoconductor, the polyether compound works as a photoconductive material, through which charge carriers which are necessary for the light decay of the photoconductor are generated and transported. However, the polyether compound itself scarcely absorbs light in the visible light range and, therefore, it is necessary to add a sensitizing dye which absorbs light in the visible light range in order to form latent electrostatic images by use of visible light.

Figure 5:
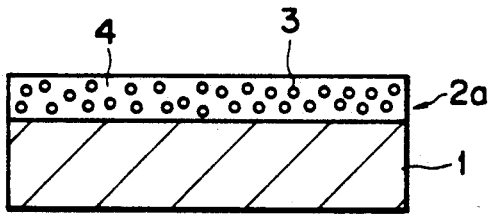
FIG. 5 is a schematic cross-sectional view of a second example of an electrophotographic photoconductor according to the present invention.

Referring to FIG. 5, there is shown an enlarged crosssectional view of another embodiment of an electrophotographic photoconductor according to the present invention. In the figure, reference numeral 1 indicates an electroconductive support. On the electroconductive support 1, there is formed a photoconductive layer 2a comprising a charge generating material 3 dispersed in a charge transporting medium 4 comprising a polyether compound and a binder agent. In this embodiment, the polyether compound and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the polyether compound not overlap in the visible light range. This is because, in order that the charge generating material 3 produce charge carriers efficiently, it is necessary that light pass through the charge transporting medium 4 and reach the surface of the charge generating material 3. Since the polyether compounds of the previously described general formula (I) do not substantially absorb light in the visible range, they can work effectively as charge transporting materials in combination with the charge generating material 3 which absorbs the light in the visible region and generates charge carriers.

Figure 6:
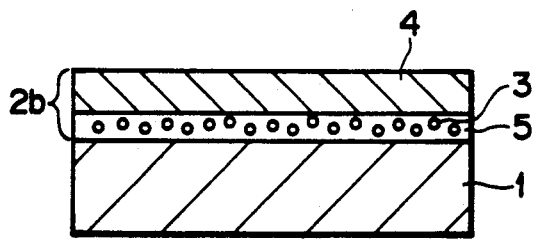
FIG. 6 is a schematic cross-sectional view of a third example of an electrophotographic photoconductor according to the present invention.

Referring to FIG. 6, there is shown an enlarged crosssectional view of a further embodiment of an electrophotographic photoconductor according to the present invention. In the figure, there is formed on an electroconductive support 1 a two-layered photoconductive layer 2b comprising a charge generation layer 5 containing the charge generating material 3, and a charge transport layer 4 containing a polyether compound of the previously described formula (I).

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, accepted and transported by the charge transport layer 4. In the charge transport layer 4, the polyether compound mainly works for transporting charge carriers. The generation and transportation of the charge carriers are performed by the same mechanism as that in the photoconductor shown in FIG. 5.

Figure 7:
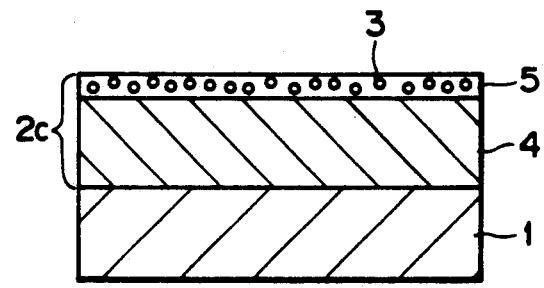
FIG. 7 is a schematic cross-sectional view of a fourth example of an electrophotographic photoconductor according to the present invention.

Referring to FIG. 7, there is shown still another embodiment of an electrophotographic photoconductor according to the present invention. In the figure, the overlaying order of the charge generation layer 5 and the charge transport layer 4 is reversed in view of the electrophotographic photoconductor as shown in FIG. 6. The mechanism of the generation and transportation of charge carriers is substantially the same as that of the photoconductor shown in FIG. 6.

Figure 8:
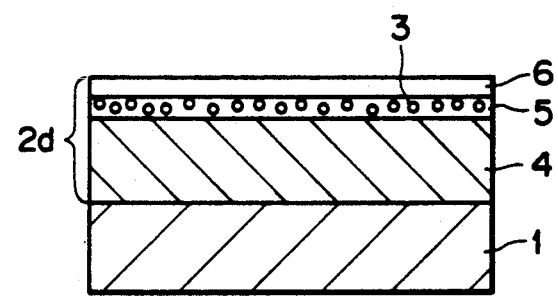
FIG. 8 is a schematic cross-sectional view of a fifth example of an electrophotographic photoconductor according to the present invention.

In the above photoconductor, a protective layer 6 may be formed on the charge generation layer 5 as shown in FIG. 8 for protecting the charge generation layer 5.

When the electrophotographic photoconductor according to the present invention as shown in FIG. 4 is prepared, at least one polyether compound of the previously described formula (I) is dispersed in a binder resin solution, and a sensitizing dye is then added to the mixture, so that a photoconductive layer coating liquid is prepared. The thus prepared photoconductive layer coating liquid is coated on an electroconductive support 1 and dried, so that a photoconductive layer 2 is formed on the electroconductive support 1.

It is preferable that the thickness of the photoconductive layer 2 be in the range of 3 to 50 μm, more preferably in the range of 5 to 20 μm. It is preferable that the amount of the polyether compound contained in the photoconductive layer 2 be in the range or 30 to 70 wt.%, more preferably about 50 wt.%.

It is preferable that the amount of the sensitizing dye contained in the photoconductive layer 2 be in the range of 0.1 to 5 wt.%, more preferably in the range of 0.5 to 3 wt.%.

Specific examples of the sensitizing dye for use in the present invention are: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl4-(N,N-dimethylaminophenyl)thiapyrylium perchlorate and benzopyrylium salts (described in Japanese Patent Publication 48-25658). These sensitizing dyes can be used alone or in combination.

The electrophotographic photoconductor shown in FIG. 5 can be obtained by dispersing finely-divided particles of the charge generating material 3 in the solution in which at least one polyether compound for use in the present invention and the binder agent are dissolved, coating the above-prepared dispersion on the electroconductive support 1 and then drying the same to form the photoconductive layer 2a.

It is preferable that the thickness of the photoconductive layer 2a be in the range of 3 to 50 μm, more preferably in the range of 5 to 20 μm. It is preferable that the amount of the polyether compound contained in the photoconductive layer 2a be in the range or 10 to 95 wt.%, more preferably in the range of 30 to 90 wt.%.

It is preferable that the amount of the charge generating material 3 contained in the photoconductive layer 2a be in the range of 0.1 to 50 wt.%, more preferably in the range of 1 to 20 wt.%.

Specific examples of the charge generating material 3 for use in the present invention are as follows: inorganic pigments such as selenium, selenium - tellurium, cadmium sulfide, cadmium sulfide - selenium and α-silicone; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). These charge generating materials may be used alone or in combination.

The electrophotographic photoconductor shown in FIG. 6 can be obtained as follows:

The charge generating material is vacuum-deposited on the electroconductive support 1, or the dispersion in which finely-divided particles of the charge generating material 3 is dispersed in an appropriate solvent, together with the binder agent when necessary, is coated on the electroconductive support 1 and dried, so that the charge generation layer 5 is formed. When necessary, the charge generation layer 5 is subjected to surface treatment by buffing and adjustment of the thickness thereof. On the thus formed charge generation layer 5, a coating solution in which at least one polyether compound and the binder agent are dissolved is coated and dried, so that the charge transport layer 4 is formed. In the charge generation layer 5, the same charge generating material as employed in the above-mentioned photoconductive layer 2a can be used.

The thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 is dispersed in an appropriate solvent together with the binder agent, it is preferable that the amount of finely-divided particles of the charge generating material 3 contained in the charge generation layer 5 be in the range of 10 to 95 wt.%, more preferably in the range of about 50 to 90 wt.%. It is preferable that the amount of the polyether compound contained in the charge transport layer 4 be in the range of 10 to 95 wt.%, more preferably in the range of 30 to 90 wt.%.

The electrophotographic photoconductor shown in FIG. 7 can be obtained as follows:

A coating solution in which the polyether compound and the binder agent are dissolved is coated on the electro-conductive support 1 and dried to form the charge transport layer 4. On the thus formed charge transport layer 4, a dispersion prepared by dispersing finely-divided particles of the charge generating material 3 in the solvent, in which the binder agent is dissolved when necessary, is coated by spray coating and dried to form the charge generation layer 5 on the charge transport layer 4. The amount ratio of components contained in the charge generation layer and charge transport layer is the same a previously described in FIG. 6.

The electrophotographic photoconductor shown in FIG. 8 can be obtained by forming a protective layer 6 on the charge generation layer 5 as obtained in FIG. 7 by spraycoating of an appropriate resin solution. As a resin employed in the protective layer 6, any of binder agents to be described later can be used.

Specific examples of the electroconductive support 1 for the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive force can be employed.

Some plasticizers may be added to the above-mentioned binder agent, when necessary. Examples of the plasticizer for use in the present invention are halogenated paraffin, polybiphenyl chloride, dimethylnaphthalene and dibutyl phthalate.

Furthermore, in the electrophotographic photoconductors according to the present invention, an adhesive layer or barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The electrophotographic photoconductors according to the present invention have the advantages in that the photosensitivity is high and the flexibility is improved.

Other features of this invention will become apparent in the course of the following description of exemplary embodiments, which are given for illustration of the invention and are not intended to be limiting thereof.

PREPARATION EXAMPLE 1-1

[Preparation of 1,5-bis(4-iodophenoxy)-3-oxapentane]

A mixture prepared by adding 3.08 g of sodium hydroxide and 40 ml of n-butanol to 15.4 g of 4-iodophenol was refluxed. 2 ml of n-butanol solution of 5.01 g of 1,5-dichloro-3-oxapentane was added dropwise to the above prepared mixture over a period of 5 minutes.

After the completion of dropping, the reaction mixture was refluxed for 13 hours, and then cooled to room temperature.

The resulting mixture was diluted with methanol, so that crystals separated out. These crystals were filtered off, washed with water and then methanol, and dried under reduced pressure. As a result, 9.73 g of colorless crystals was obtained in the form of needles.

These crystals were recrystallized from a mixed solvent of toluene and n-hexane, so that 8.34 g of 1,5-bis(4-iodophenoxy)-3-oxapentane precipitated as colorless crystals in the form of plates. The melting point of the above compound was 139.5° to 140.5° C.

The results of the elemental analysis of the thus obtained compound were as follows:

|  | % C | % H |
|---|---|---|
| Calculated | 37.67 | 3.17 |
| Found | 37.59 | 2.92 |

The above calculation was based on the formula for 1,5-bis(4-iodophenoxy)-3-oxapentane of $C_{16}H_{16}I_2O_3$.

FIG. 1 shows an infrared spectrum of 1,5-bis(4-iodophenoxy)-3-oxapentane, taken by use of a KBr tablet.

PREPARATION EXAMPLE 1-2

[Preparation of 1,5-bis(4'-iodobiphenylyl-4-oxy)-3oxapentane]

A mixture prepared by adding 0.45 g of sodium hydroxide and 20 ml of n-butanol to 2.96 g of 4-(4-iodophenyl)phenol was refluxed. 1 ml of n-butanol solution of 0.79 g of 1,5-dichloro-3-oxapentane was added dropwise to the above prepared mixture over a period of 15 minutes.

After the completion of dropping, the reaction mixture was refluxed for 18 hours, and then cooled to room temperature, so that crystals separated out. These crystals were filtered off, washed with water and then methanol, and dried under reduced pressure. As a result, 2.30 g of colorless crystals was obtained in the form of needles.

These crystals were washed with heated ethanol, so that 2.15 g of 1,5-bis(4'-iodobiphenylyl-4-oxy)-3-oxapentane precipitated as colorless crystals in the form of needles. The melting point of the above compound was 230.0° to 231.0° C.

The results of the elemental analysis of the thus obtained compound were as follows:

|  | % C | % H |
|---|---|---|
| Calculated | 50.77 | 3.66 |
| Found | 50.67 | 3.40 |

The above calculation was based on the formula for 1,5-bis(4'-iodobiphenylyl-4-oxy)-3-oxapentane of $C_{28}H_{24}I_2O_3$.

Figure 2:
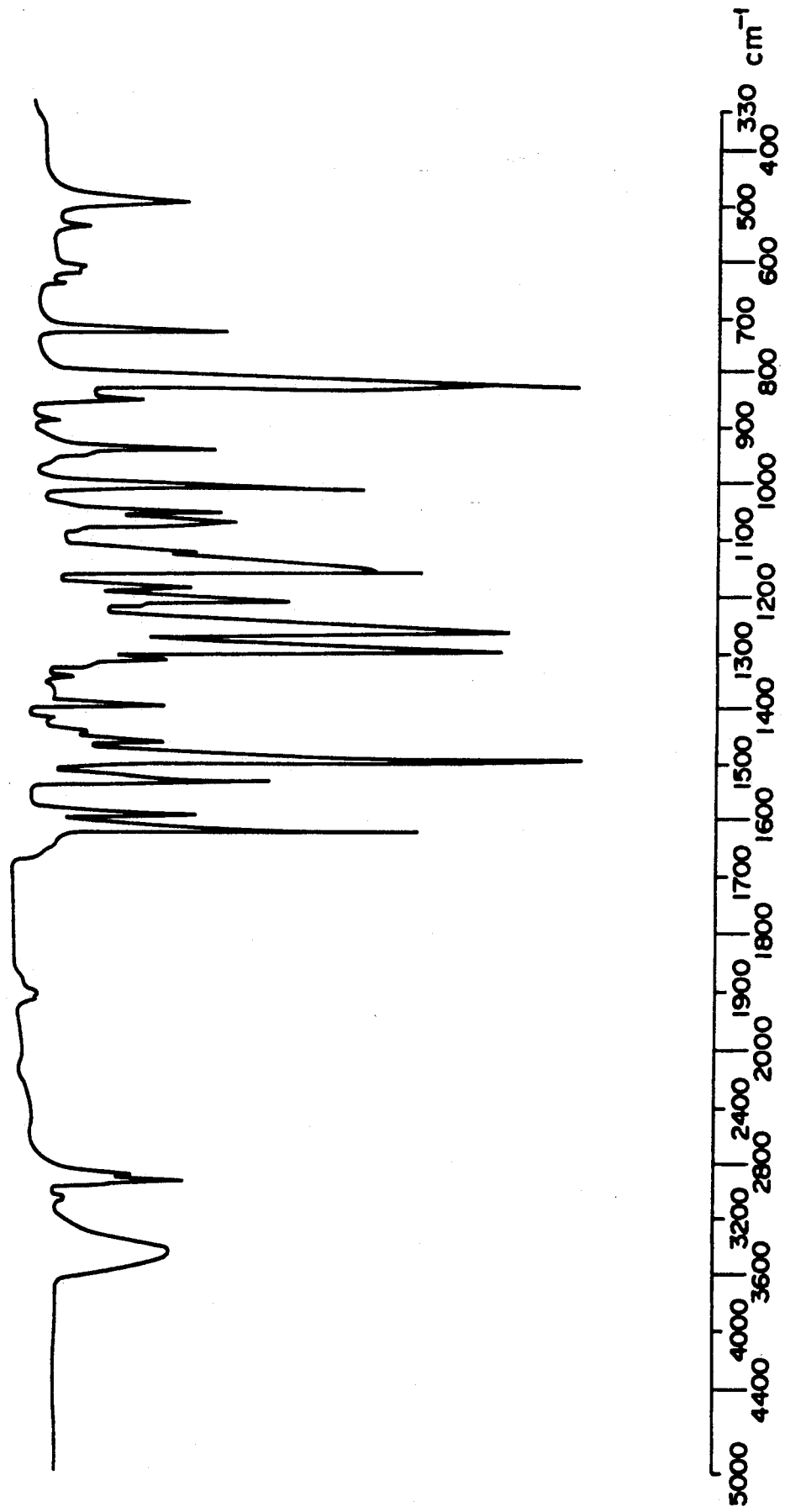

FIG. 2 shows an infrared spectrum of 1,5-bis(4'-iodobiphenylyl-4-oxy)-3-oxapentane, taken by use of a KBr tablet.

PREPARATION EXAMPLE 2-1

[Synthesis of 1,5-bis(4'-N,N-bis(4-methylphenyl)-aminobiphenylyl-4-oxy}-3-oxapentane -- Polyether Compound No. 12 in Table 1]

2.0 g of 1,5-bis(4'-iodobiphenylyl-4-oxy)-3-oxapentane prepared in Preparation Example 1-2, 1.79 g of 4,4'-dimethyldiphenylamine, 1.25 g of potassium carbonate and 0.25 g of copper particles were added to 20 ml of nitrobenzene. This mixture was refluxed in a stream of nitrogen for 10 hours. After the mixture was cooled to room temperature, the resulting insoluble material of the mixture was removed by filtration together with Celite and nitrobenzene was removed therefrom.

The residue was extracted with toluene, washed with water and dried. Thereafter, the thus obtained extract was concentrated under the reduced pressure, so that oily dark brown material was obtained.

This oily material was subjected to column chromatography using silica gel and toluene as a carrier and an eluting solution, respectively. The product was recrystallized twice from a mixed solvent of ethyl acetate and ethanol, so that 0.60 g of 1,5-bis{4'-N,N-bis(4-methylphenyl)-aminobiphenylyl-4-oxy}-3-oxapentane precipitated as white crystals in the form of grains. The melting point of the compound, namely the endothermic peak in accordance with TG-DSC, was 75° C.

The results of the elemental analysis of the thus obtained compound were as follows:

|  | % C | % H | % N |
|---|---|---|---|
| Calculated | 83.95 | 6.56 | 3.50 |
| Found | 83.86 | 6.72 | 3.38 |

The above calculation was based on the formula for 1,5bis{4'-N,N-bis(4-methylphenyl)-aminobiphenylyl-4-oxy}-3oxapentane of $C_{56}H_{52}N_2O_3$.

Figure 3:
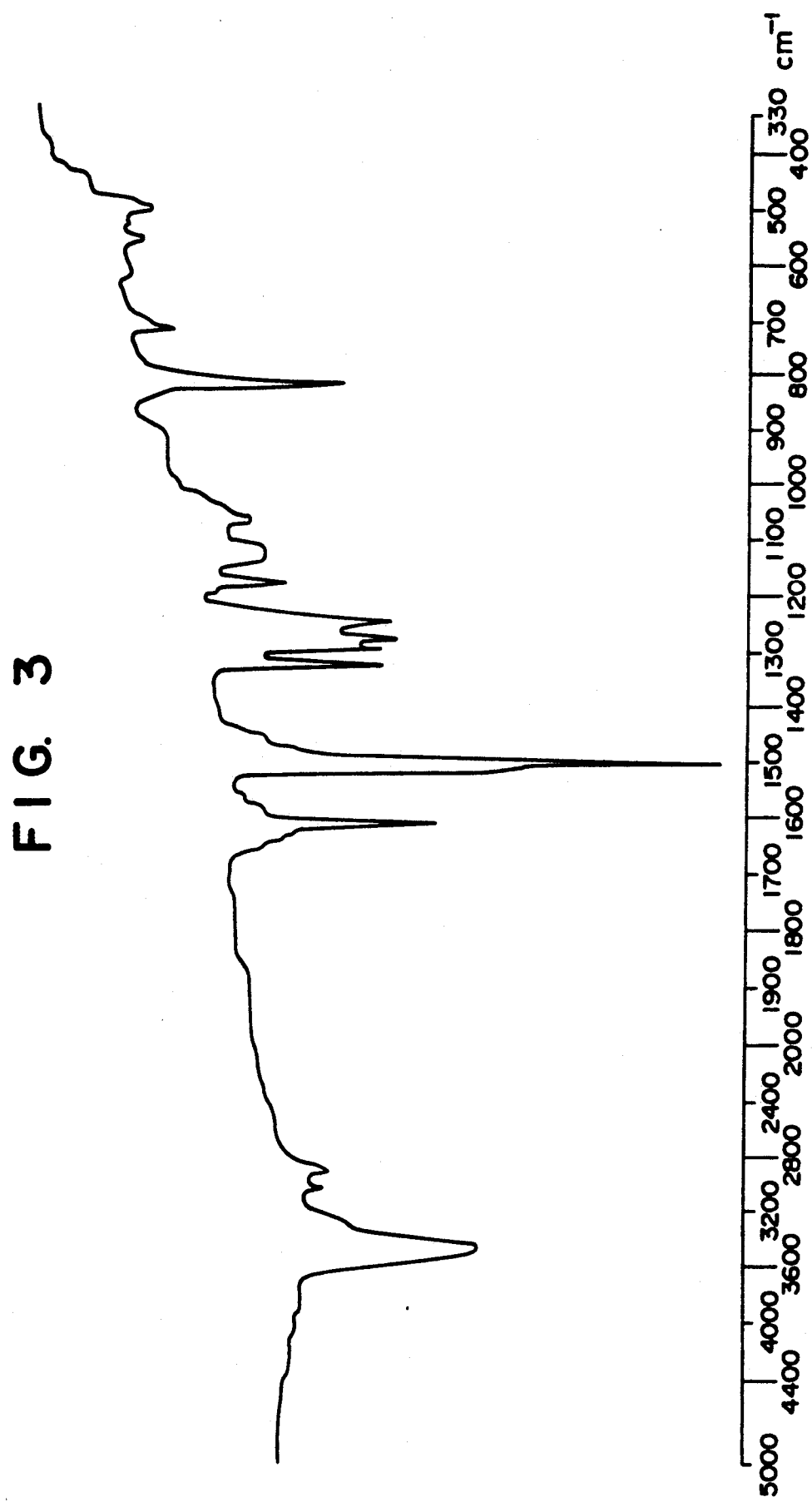
FIG. 3 is an IR spectrum of an polyether compound according to the present invention.

FIG. 3 shows an infrared spectrum of 1,5-bis{4'-N,Nbis(4-methylphenyl)-aminophenylyl-4-oxy}-3-oxapentane, (polyether compound No. 12 in Table 1) taken by use of a KBr tablet.

PREPARATION EXAMPLE 2-2

[Synthesis of 1,5-bis(4-N,N-di-p-tolylaminophenoxy)-3-oxapentane -- Polyether Compound No. 4 in Table 1]

5.10 g of 1,5-bis(4-iodophenoxy)-3-oxapentane prepared in Preparation Example 1-1, 4.34 g of 4,4'-dimethyl diphenylamine, 4.15 g of potassium carbonate and 0.83 g of copper particles were added to 60 ml of nitrobenzene. This mixture was refluxed in a stream of nitrogen for 16 hours. After the mixture was cooled to room temperature, the resulting insoluble material of the mixture was removed by filtration together with Celite and nitrobenzene was removed therefrom.

The residue was extracted with toluene, washed with water and dried. Thereafter, the thus obtained extract was concentrated under the reduced pressure, so that oily dark brown material was obtained.

This oily material was subjected to column chromatography using silica gel and toluene as carrier and an eluting solution, respectively, so that 2.27 g of colorless oily 1,5-bis(4-N,N-di-p-tolylamino-phenoxy)-3-oxapentane was obtained.

The results of the elemental analysis of the thus obtained compound were as follows:

|  | % C | % H | % N |
|---|---|---|---|
| Calculated | 81.44 | 6.85 | 4.32 |
| Found | 81.22 | 6.78 | 4.33 |

The above calculation was based on the formula for 1,5-bis(4-N,N-di-p-tolylaminophenoxy)-3-oxapentane of $C_{44}H_{44}N_2O_3$.

FIG. 4 shows an infrared spectrum of 1,5-bis(4-N,N-di-p-tolylaminophenoxy)-3-oxapentane (polyether compound No. 4 in Table 1), taken by use of a KBr tablet.

EXAMPLE 1

7.5 parts by weight of a bisazo compound having the following formula and 500 parts by weight of a 0.5% tetrahydrofuran solution of a polyester resin (Trademark "Vylon 200" made by Toyobo Company, Ltd.) were dispersed and ground in a ball mill. The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

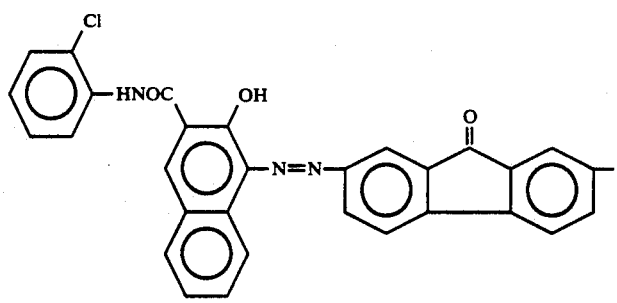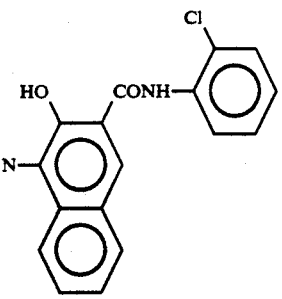

One part by weight of 1,5-bis{4'-N,N-bis(4-methylphenyl)aminobiphenylyl-4-oxy}-3-oxapentane (polyether compound No. 12 in Table 1) prepared in the above-mentioned Preparation Example 2-1 was dissolved in a resin solution consisting of 1 part by weight of polycarbonate resin (Trademark "Panlite K-1300" made by Teijin Limited.) and 8 parts by weight of tetrahydrofuran. This solution was coated on the above formed charge generation layer by a doctor blade and then dried at 80° C. for 2 minutes and then at 120° C. for 5 minutes, so that a charge transport layer having a thickness of about 20 μm was formed on the charge generation layer. Thus a two-layered type electrophotographic photoconductor No. 1 according to the present invention was prepared.

EXAMPLE 2

76 parts by weight of Diane Blue (C.I. Pigment Blue 25, CI21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

2 parts by weight of 1,5-bis{4'-N,N-bis(4-methylphenyl)aminobiphenylyl-4-oxy}-3-oxapentane (polyether compound No. 12 in Table 1) prepared in the above-mentioned Preparation Example 2-1, 2 parts by weight of polycarbonate resin (Trademark "Panlite K-1300" made by Teijin Limited.) and 16 parts by weight of tetrahydrofuran were mixed to form a solution. This solution was coated on the above formed charge generation layer by a doctor blade and then dried at 80° C. for 2 minutes and then at 120° C. for 5 minutes, so that a charge transport layer having a thickness of about 20 μm was formed on the charge generation layer. Thus a two-layered type electrophotographic photoconductor No. 2 according to the present invention was prepared.

EXAMPLES 3 TO 22

The procedure for preparation of the two-layered type electrophotographic photoconductor No. 2 in Example 2 wa repeated except that Diane Blue serving as a charge generating material and the polyether compound No. 12 serving as a charge transporting material employed in Example 2 were replaced by the respective charge generating materials and charge transporting materials listed in the following Table 2, whereby two-layered type electrophotographic photoconductors No. 3 to No. 22 according to the present invention were prepared.

TABLE 2

| Photo-conductor | Charge Generating Material | Charge Transporting Material (Polyether Compound No.) |
|---|---|---|
| 1 | (bisazo naphthol structure with OCH₃ groups and phenyl CONH end groups) | 12 |
| 2 | (bisazo naphthol structure with Cl groups and phenyl CONH end groups) | 12 |
| 3 | (bisazo stilbene structure with 2,4-dimethylphenyl CONH end groups) (hereinafter referred to as P-1) | 12 |

TABLE 2-continued

| Photo-conductor | Charge Generating Material | Charge Transporting Material (Polyether Compound No.) |
|---|---|---|
| 4 | (bisazo naphthol structure with CONH-phenyl groups linked via N=N–phenyl–C(=O)–O–C(=O)–phenyl–N=N) | 12 |
| 5 | (bisazo naphthol structure with CONH-(2-chlorophenyl) groups linked via N=N to fluorenone) (hereinafter referred to as P-2) | 12 |
| 6 | (polymeric azo compound with CONH-(2-ethylphenyl), naphthol, and indole units, repeating unit n=3) | 12 |

TABLE 2-continued

| Photo-conductor | Charge Generating Material | | Charge Transporting Material (Polyether Compound No.) |
|---|---|---|---|
| 7 | β-type Copper Phthalocyanine | | 12 |
| 8 | (azo compound with OCH₃ substituents) | | 4 |
| 9 | (azo compound with Cl substituents) | | 4 |
| 10 | | P-1 | 4 |
| 11 | | P-2 | 4 |
| 12 | | P-1 | 13 |
| 13 | | P-2 | 13 |
| 14 | | P-1 | 17 |
| 15 | | P-2 | 17 |
| 16 | | P-1 | 18 |
| 17 | | P-2 | 18 |
| 18 | | P-1 | 11 |
| 19 | | P-2 | 11 |
| 20 | | P-1 | 6 |
| 21 | | P-2 | 6 |

EXAMPLE 23

Selenium was vacuum-deposited on an aluminum plate having a thickness of 300 μm, so that a charge generation layer having a thickness of about 1 μm was formed on the aluminum plate.

2 parts by weight of 1,5-bis{4'-N,N-bis(4-methylphenyl)aminobiphenylyl-4-oxy}-3-oxapentane (polyether compound No. 12 in Table 1) prepared in the above-mentioned Preparation Example 2-1, 3 parts by weight of polyester resin (Trademark "Polyester Adhesive 49000" made by Du Pont de Nemours, E.I. & Co.) and 45 parts by weight of tetrahydrofuran were mixed to form a solution. This solution was coated on the above formed charge generation layer by a doctor blade, dried at room temperature, and then dried under reduced pressure, so that a charge transport layer with a thickness of about 10 μm was formed on the charge generation layer. Thus a two-layered type electrophotographic photoconductor No. 23 according to the present invention was prepared.

EXAMPLE 24

The procedure for preparation of the two-layered electrophotographic photoconductor No. 23 in Example 23 was repeated except that a charge generation layer with a thickness of about 0.6 μm was formed on the same aluminum plate as employed in Example 23 by deposition of the following perylene pigment instead of selenium, so that a two-layered electrophotographic photoconductor No. 24 according to the present invention was prepared.

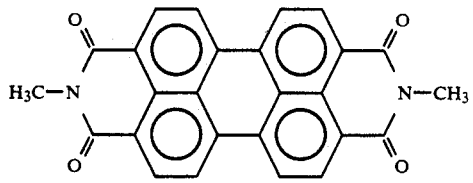

EXAMPLE 25

A mixture of 1 part by weight of the same Diane Blue as employed in Example 2 and 158 parts by weight of tetrahydrofuran was dispersed and ground in ball mill to form a dispersion. To the thus formed dispersion, 12 parts by weight of the polyether compound No. 12 in Table 1 and 18 parts by weight of polyester resin (Trademark "Polyester Adhesive 49000" made by Du Pont de Nemours, E.I. & Co.) were added to form a solution. This solution was coated on an aluminum-deposited polyester film by a doctor blade, and dried at 100° C. for 30 minutes, so that a photoconductive layer having a thickness of about 16 μm was formed on the electroconductive support. Thus, an electrophotographic photoconductor No. 25 according to the present invention was prepared.

EXAMPLE 26

2 parts by weight of 1,5-bis{4'-N,N-bis(4-methylphenyl)aminobiphenylyl-4-oxy}-3-oxapentane (polyether compound No. 12 in Table 1) prepared in the above-mentioned Preparation Example 2-1, 2 parts by weight of polycarbonate resin (Trademark "Panlite K-1300" made by Teijin Limited.) and 16 parts by weight of tetrahydrofuran were mixed to form a solution. This solution was coated on the same aluminum surface of an aluminum-deposited polyester film by a doctor blade and dried, so that a charge transport layer with a thickness of about 20 μm was formed on the aluminum-deposited polyester film.

A mixture of 13.5 parts by weight of bisazo pigment (P-2), 5.4 parts by weight of polyvinyl butyral (Trademark "XYHL" made by Union Carbide Japan K.K.), 680 parts by weight of tetrahydrofuran and 1020 parts by weight of ethyl cellosolve was dispersed and ground in a ball mill. To this dispersion, 1700 parts by weight of additional ethyl cellosolve was added to form a solution. This solution was coated on the above formed charge transport layer by spray coating and dried at 100° C. for 10 minutes, so that a charge generation layer having a thickness of about 0.2 μm was formed on the charge transport layer.

A methanol - n-butanol based solution of a polyamide resin (Trademark "CM-8000" made by Toray Silicone Co., Ltd.) was coated on the above formed charge generation layer by spray coating and dried at 120° C. for 30 minutes, so that a protective layer having a thickness of about 0.5 μm was formed on the charge generation layer. Thus, an electrophotographic photoconductor No. 25 according to the present invention was prepared.

Each of the thus prepared electrophotographic photoconductors No. 1 through No. 26 according to the present invention was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E_{\frac{1}{2}}$(lux.-sec) required to reduce the initial surface potential Vpo (V) to ½ the initial surface potential Vpo (V) was measured. The results are shown in Table 3.

TABLE 3

| Photoconductor No. | Vpo (V) | $E_{\frac{1}{2}}$ (lux · sec) |
|---|---|---|
| 1 | −1057 | 0.99 |
| 2 | −1010 | 1.72 |
| 3 | −980 | 1.40 |
| 4 | −1210 | 1.18 |
| 5 | −1330 | 2.30 |
| 6 | −1060 | 0.99 |
| 7 | −1110 | 2.01 |
| 8 | −1310 | 1.80 |
| 9 | −1290 | 1.70 |
| 10 | −1020 | 1.45 |
| 11 | −1270 | 1.12 |
| 12 | −1180 | 0.82 |
| 13 | −1220 | 1.20 |
| 14 | −980 | 1.01 |
| 15 | −1010 | 1.23 |
| 16 | −1120 | 0.97 |
| 17 | −1390 | 1.18 |
| 18 | −1230 | 1.00 |
| 19 | −990 | 1.21 |
| 20 | −1020 | 0.90 |
| 21 | −1270 | 1.10 |
| 22 | −940 | 0.81 |
| 23 | −720 | 2.40 |
| 24 | −1370 | 3.21 |
| 25 | +1290 | 2.40 |

TABLE 3-continued

| Photoconductor No. | Vpo (V) | E_{1/2} (lux · sec) |
|---|---|---|
| 26 | +1130 | 0.97 |

The electrophotographic photoconductors according to the present invention comprise a photoconductive layer comprising any of the above-mentioned specific polyether compounds serving as an organic photoconductive material, so that the resistance to heat and mechanical shocks of the photoconductor can be improved as well as the photoconductive properties thereof. Furthermore, the photoconductors according to the present invention can be manufactured at low cost.

What is claimed is:

1. A charge transporting material having formula (I):

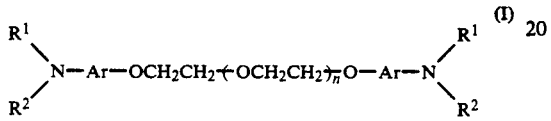

wherein Ar represents a para-substituted phenylene group or a para-substituted biphenylene group; $R^1$ and $R^2$ each represent an aryl group which may have a substituent, selected from the group consisting of
 (1) a halogen, a cyano group, a nitro group,
 (2) a $C_2$-$C_{12}$ alkyl group which may have a substituent selected from the group consisting of a fluorine atom, an hydroxyl group, a cyano group, an alkoxyl group having 1 to 4 carbon atoms, and a phenyl group which may be substituted by a halogen, an alkyl group having 1 to 4 carbon atoms or an alkoxyl group having 1 to 4 carbon atoms,
 (3) an alkoxyl group represented by $-OR^3$, in which $R^3$ represents the same alkyl group as defined in (2);
 (4) an aryloxy group which may be substituted by an alkoxyl group having 1 to 4 carbon atoms, an alkyl group having 1 to 4 carbon atoms or a halogen;
 (5) an alkylmercapto group represented by $-SR^4$, in which $R^4$ represents the same alkyl group as defined in (2);
 (6) $-NR^5R^6$, in which $R^5$ and $R^6$ independently represent hydrogen, the same alkyl group as defined in (2) or aryl group which may be substituted by an alkoxyl group having 1 to 4 carbon atoms, an alkyl group having 1 to 4 carbon atoms or a halogen, $R^5$ and $R^6$ may form a ring in combination, or in combination with carbon atoms on the aryl group;
 (7) an alkylenedioxy group or alkylenedithio group; and n is an integer of 1 to 4.

2. A polyether compound having formula (II):

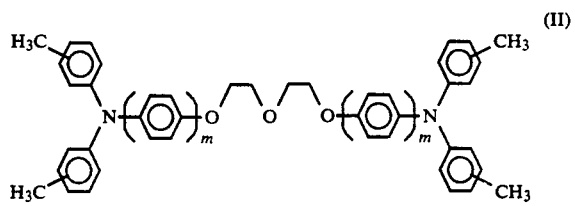

wherein m is an integer of 1 or 2.

3. The polyether compound, which is selected from the group consisting of:

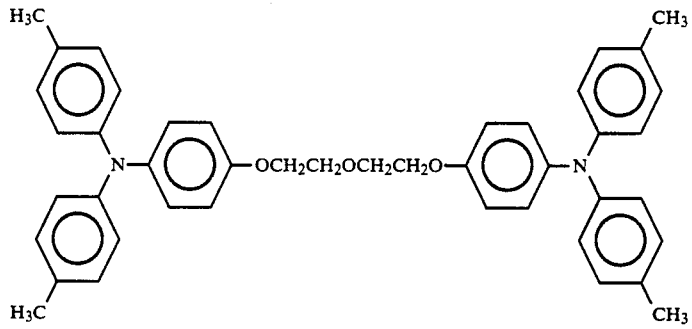

and

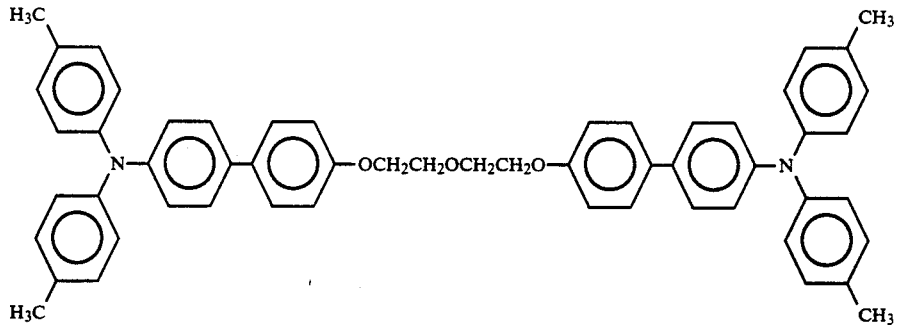

UNITED STATES PATENT AND TRADEMARK OFFICE
CERTIFICATE OF CORRECTION

PATENT NO. : 5,248,826

DATED : September 28, 1993

INVENTOR(S) : Masaomi Sasaki, et al

It is certified that error appears in the above-identified patent and that said Letters Patent is hereby corrected as shown below:

Column 1, Line 23, "charge The uniformly" should read --charge. The uniformly--

Column 3, Line 61, "wherein" should read --wherein:--

Column 3, Line 67, "of an polyether" should read --of a polyether--

Column 4, Line 47, "an hydroxyl" should read --a hydroxyl--

Column 6, Line 3, "halogen $R^5$ and $R^6$" should read --halogen. $R^5$ and $R^6$--

Column 9, Line 62, "[VII)" should read --(VII)--

UNITED STATES PATENT AND TRADEMARK OFFICE
CERTIFICATE OF CORRECTION

PATENT NO. : 5,248,826

DATED : September 28, 1993

INVENTOR(S) : Masaomi Sasaki, et al

It is certified that error appears in the above-identified patent and that said Letters Patent is hereby corrected as shown below:

Column 12, Line 15, "in the range or" should read --in the range of--

Column 12, Line 45, "54-14967}" should read --54-14967)--

Column 15, Line 26, "1,5-bis(4'-iodobiphenylyl-4-oxy)" should read --1,5-bis{4'

Column 27, Line 30, "a $C_2-C_{12}$" should read --a $C_1-C_{12}$--

UNITED STATES PATENT AND TRADEMARK OFFICE
CERTIFICATE OF CORRECTION

Page 3 of 3

PATENT NO. : 5,248,826
DATED : September 28, 1993
INVENTOR(S) : Masaomi Sasaki, et. al.

It is certified that error appears in the above-indentified patent and that said Letters Patent is hereby corrected as shown below:

Column 27, Line 32, "an hydroxyl" should read --a hydroxyl--

Signed and Sealed this

Twenty-fourth Day of January, 1995

Attest:

Attesting Officer

BRUCE LEHMAN

Commissioner of Patents and Trademarks